US011452802B2

(12) United States Patent
Murata (10) Patent No.: US 11,452,802 B2
(45) Date of Patent: Sep. 27, 2022

(54) PERFUSION DEVICE AND METHOD FOR OPERATING SAME

(71) Applicants:Satoru Murata, Tokyo (JP); KOSEI ADVANCE CO., LTD., Saitama (JP)

(72) Inventor: Satoru Murata, Tokyo (JP)

(73) Assignees: Satoru Murata, Tokyo (JP); KOSEI ADVANCE CO., LTD., Saitama (JP)

( * ) Notice: Subject to any disclaimer, the term of this patent is extended or adjusted under 35 U.S.C. 154(b) by 465 days.

(21) Appl. No.: 16/622,386

(22) PCT Filed: Jun. 12, 2018

(86) PCT No.: PCT/JP2018/022479
§ 371 (c)(1),
(2) Date: Dec. 13, 2019

(87) PCT Pub. No.: WO2018/230577
PCT Pub. Date: Dec. 20, 2018

(65) Prior Publication Data
US 2020/0197588 A1 Jun. 25, 2020

(30) Foreign Application Priority Data
Jun. 13, 2017 (JP) .............................. JP2017-115634

(51) Int. Cl.
*A61M 1/16* (2006.01)
*A61M 1/36* (2006.01)
(52) U.S. Cl.
CPC ........ *A61M 1/1621* (2014.02); *A61M 1/1601* (2014.02); *A61M 1/3621* (2013.01)
(58) Field of Classification Search
CPC .... A61M 1/0281; A61M 1/16; A61M 1/1601; A61M 1/1621; A61M 1/3615; A61M 1/3621; A61M 1/3659
See application file for complete search history.

(56) References Cited

U.S. PATENT DOCUMENTS

| 5,817,046 A * | 10/1998 | Glickman .......... A61M 25/1011 604/6.11 |
| 6,287,273 B1 * | 9/2001 | Allers ................ A61M 1/3613 604/27 |
| 2003/0153871 A1 | 8/2003 | Kumazaki et al. |

FOREIGN PATENT DOCUMENTS

| JP | 2003-102829 A | 4/2003 |
| JP | 4024506 B2 | 12/2007 |

OTHER PUBLICATIONS

Murata, Satoru, et al. (Oct. 25, 2002). Development and Clinical Assessment of Isolated Pelvic Perfusion. Journal of Nippon Medical School, 69(5), 468-470, The Medical Association of Nippon Medical School, Japan, https://www.jstage.jst.go.jp/article/jnms/69/5/69_5_468/_pdf Cited in the specification, with partial translation.
(Continued)

*Primary Examiner* — Dirk R Bass
(74) *Attorney, Agent, or Firm* — Michael Best & Friedrich LLP (57) ABSTRACT

A negative-balanced isolated pelvic perfusion method, in which a drug is administered into the closed pelvis while keeping the volume of suction from the vein larger than that of injection into the artery, does not require allogeneic blood transfusion. A perfusion device is for recovering a liquid containing a drug and/or blood from a tube connecting to the inferior vena cava and for injecting the liquid obtained into a tube connecting to the artery, provided with a unit for closing the inside of the pelvis by including a unit for blocking the artery from the heart to the pelvis, a unit for blocking the inferior vena cava from the pelvis to the heart, and a unit for blocking a blood flow from the pelvis to the lower limbs. The perfusion device is provided with a pelvic perfusion unit equipped with a reservoir, an autotransfusion unit, and a dialysis unit.

6 Claims, 2 Drawing Sheets

(56) References Cited

OTHER PUBLICATIONS

International Search Report dated Aug. 21, 2018 for the corresponding PCT Application No. PCT/JP2018/022479, with translation.

* cited by examiner

PERFUSION DEVICE AND METHOD FOR OPERATING SAME

CROSS-REFERENCE TO RELATED APPLICATIONS

This application is entering the National Phase of International Application No. PCT/JP2018/022479, filed on Jun. 12, 2018. Further, this application claims priority form Japanese Patent Application No. JP 2017-115634, filed on Jun. 13, 2017, the entire contents of which are hereby incorporated by reference.

TECHNICAL FIELD

The present invention relates to a perfusion device, and a method for operating the perfusion device, and in particular, a perfusion device applied in the human pelvis, and a method for operating the perfusion device.

BACKGROUND ART

Systemic chemotherapy or intra-arterial infusion therapy has been widely performed for pelvic advanced malignant tumor and pelvic recurrence cases. In such a therapy method, since the administered anticancer agent circulates from the vein to the whole body, the dosage has to be reduced from the viewpoint of the side effects. In most of anticancer agents, the dosage correlates to the therapeutic effect, and therefore, it is ideal firstly to increase the dosage and secondly to increase the administration time in order to increase the therapeutic effect.

In view of this, "anticancer-agent isolated pelvic perfusion therapy (isolated pelvic perfusion)" has been devised. This therapy is a method in which the aorta and the inferior vena cava are temporarily occluded with the use of balloon catheters by a radiological procedure (technique for vascular imaging) and a surgical procedure, a blood flow of the lower limbs is temporarily blocked by a pair of tourniquets at the same time to block a blood flow in the pelvis part, an anticancer agent is injected into the pelvis part, and sucked, the anticancer agent concentration in the pelvis is kept high, and the leakage of the anticancer agent to the outside of the pelvis is suppressed as far as possible.

However, since a developed collateral circulation is present in the pelvis, in the anticancer-agent isolated pelvic perfusion therapy, around 40% of the anticancer agent leaks to the whole-body system in around 10 minutes from the start of perfusion. Further, since there is no unit to remove the anticancer agent present in the pelvis after completion of the perfusion therapy, the total dosage of the anticancer agent eventually flows into the whole-body system, and therefore, the normal amount of anticancer agent, which is similar to the amount in a case where the pelvis is not in a closed circulation, was only able to be used after all.

In view of this, the present inventors, et al. has proposed a negative-balanced isolated pelvic perfusion (NIPP) method in which for the purpose of preventing the leakage of anticancer agent to the developed collateral circulation, the venous pressure in the pelvis is set to be lower than the venous pressure outside the pelvis, and the anticancer agent in the pelvis is removed with a dialysis device in a closed circulation immediately after completion of the treatment (Patent Literature 1, and Non Patent Literature 1).

In this method, at first, a 9-French sheath and a 6-French sheath each with side holes and a thick side arm are inserted into the left and right femoral arteries, and a 5-French balloon catheter is inserted so that a balloon is placed immediately above the aortic bifurcation. Further, a 9-French sheath and a 5-French sheath are inserted into the left and right femoral veins, and a 6-French balloon catheter is inserted so that a balloon is placed immediately above the common iliac confluence point in the inferior vena cava. A catheter and sheaths are connected to a cardiopulmonary circulation device (pump) with a tube to form a perfusion system. By applying pressure with a pair of tourniquets, the blood flow to the lower limbs is temporarily blocked, and after administration of heparin, two balloon catheters are inflated to occlude the aorta and vena cava. By using a pump, an anticancer agent is injected and sucked, and this procedure is continuously performed for 30 minutes. At this time, the volume of suction from the vein is set slightly larger than the volume of injection into the artery. After the anticancer-agent perfusion therapy, perfusion is performed with a dialysis device in order to remove the anticancer agent in the pelvis.

According to this method, since this method is a method for suppressing the leakage of an anticancer agent into the systemic circulation by setting the suction rate to be higher than the injection rate, the leakage of the anticancer agent into the systemic circulation can be reduced.

CITATION LIST

Patent Literature

PATENT LITERATURE 1: JP 4024506 B1

Non Patent Literature

NON PATENT LITERATURE 1: Satoru Murata, and 11 others, "Development and Clinical Assessment of Isolated Pelvic Perfusion", [online], Oct. 25, 2002, The Medical Association of Nippon Medical School, [Searched on Jan. 20, 2017], Internet <URL: https://www.jstagejst.go.jp/article/jnms/69/5/69_5_468/_pdf>

SUMMARY OF INVENTION

Technical Problem

However, in the methods of Patent Literature 1 and Non Patent Literature 1, in order to set the venous pressure in the pelvis lower than the venous pressure outside the pelvis, the volume of suction from the vein is set slightly larger than the volume of injection into the artery, and as a result, 800 ml of blood is required for the transfusion to a patient because the patient loses a large amount of blood.

Further, around 20% of the used anticancer agent still leaks into the whole body, and therefore, there is still a risk of exacerbation of the renal disorder for a patient with moderate to severe impaired renal function, and those methods have not been applied to a patient with impaired renal function.

The present invention is made in consideration of the problems described above, and an object of the present invention is to provide a perfusion device that does not require allogeneic blood transfusion and a method for operating the perfusion device, in a negative-balanced isolated pelvic perfusion method, in which a drug is administered into the closed human pelvis while keeping the volume of suction from the vein larger than the volume of injection into the artery.

Another object of the present invention is to provide a perfusion device that can further reduce the volume of drug leakage into the whole body and a method for operating the perfusion device, in a negative-balanced isolated pelvic perfusion method, in which a drug is administered into the closed human pelvis.

Solution to Problem

According to the method for operating a perfusion device of the present invention, the problems described above are solved by providing a perfusion device for recovering a liquid containing drugs and/or blood from a drainage tube for connecting to the inferior vena cava and for injecting the liquid finally obtained into a return tube for connecting to the artery, which is provided with a pelvic area closing unit for closing the inside of the pelvis from the outside of the pelvis by including an artery occlusion unit for blocking a blood flow in the artery from the heart side to the pelvis side, an inferior vena cava occlusion unit for blocking a blood flow of the inferior vena cava from the pelvis side to the heart side, and a lower-limb side blocking unit for blocking a blood flow from the pelvis side to the lower-limb side, including: a pelvic perfusion unit equipped with a perfusion pump for recovering the liquid from the drainage tube and injecting the liquid finally obtained into the return tube, a reservoir for storing a part of the liquid from the drainage tube, and a perfusion tube constituting a flow path from the drainage tube to the return tube through the perfusion pump and the reservoir; an autotransfusion unit equipped with a transfusion device tube, an autotransfusion device connected to the transfusion device tube, and an autotransfusion tube for connecting to the vein outside the pelvis; a dialysis unit equipped with a dialysis drainage tube and a dialysis return tube each with the tip placed at a position closer to the heart side than the inferior vena cava occlusion unit of the inferior vena cava, an extracorporeal hemodialysis device connectable to the dialysis drainage tube and the dialysis return tube, and a dialysis tube constituting a flow path from the dialysis drainage tube to the dialysis return tube through the hemodialysis device; a transfusion device switching unit for switching a connection of the transfusion device tube to the downstream side of the reservoir of the perfusion tube, between the reservoir of the perfusion tube and the return tube; and a dialysis device switching unit for switching a connection of the dialysis tube to the drainage tube and the return tube in the pelvis, between the reservoir of the perfusion tube and the return tube.

According to the method for operating a perfusion device of the present invention, the problems described above are solved by performing a method for operating a perfusion device for recovering a liquid containing drugs and/or blood from a drainage tube for connecting to the inferior vena cava and for injecting the liquid finally obtained into a return tube for connecting to the artery, which is provided with a pelvic area closing unit for closing the inside of the pelvis from the outside of the pelvis by including an artery occlusion unit for blocking a blood flow in the artery from the heart side to the pelvis side, an inferior vena cava occlusion unit for blocking a blood flow of the inferior vena cava from the pelvis side to the heart side, and a lower-limb side blocking unit for blocking a blood flow from the pelvis side to the lower-limb side, in which the perfusion device includes: a pelvic perfusion unit equipped with a perfusion pump for recovering the liquid from the drainage tube and injecting the liquid finally obtained into the return tube, a reservoir for storing a part of the liquid from the drainage tube, and a perfusion tube constituting a flow path from the drainage tube to the return tube through the perfusion pump and the reservoir; an autotransfusion unit equipped with a transfusion device tube, an autotransfusion device connected to the transfusion device tube, and an autotransfusion tube for connecting to the vein outside the pelvis; a dialysis unit equipped with a dialysis drainage tube and a dialysis return tube each with the tip placed at a position closer to the heart side than the inferior vena cava occlusion unit of the inferior vena cava, an extracorporeal hemodialysis device connectable to the dialysis drainage tube and the dialysis return tube, and a dialysis tube constituting a flow path from the dialysis drainage tube to the dialysis return tube through the hemodialysis device; a transfusion device switching unit for switching a connection of the transfusion device tube to the downstream side of the reservoir of the perfusion tube, between the reservoir of the perfusion tube and the return tube; and a dialysis device switching unit for switching a connection of the dialysis tube to the drainage tube and the return tube in the pelvis, between the reservoir of the perfusion tube and the return tube, and the method performs: an operation process of a perfusion pump for the pelvis and a dialysis device for the outside of the pelvis, in which the perfusion pump operates in a state of being connected to the drainage tube and the return tube in the pelvis, and the hemodialysis device operates in a state of being connected to the dialysis drainage tube and the dialysis return tube; an operation process of a postoperative flow path switching unit, in which the transfusion device switching unit and the dialysis device switching unit operate; and an operation process of a postoperative blood transfusion device and a dialysis device for the inside of the pelvis, in which the autotransfusion device operates in a state of being connected to the downstream side of the reservoir of the perfusion tube, and the hemodialysis device operates in a state of being connected to the drainage tube and the return tube in the pelvis.

As described above, the perfusion device is provided with a transfusion device switching unit for switching a connection of the transfusion device tube to the downstream side of the reservoir of the perfusion tube, between the reservoir of the perfusion tube and the return tube, and therefore, a liquid containing drugs and/or blood stored in the reservoir is purified by performing perfusion in the closed pelvis with an autotransfusion device after completion of the perfusion in the pelvis, and the liquid finally obtained can be returned into the body of a patient.

Therefore, for example, in the negative-balanced isolated pelvic perfusion method in which the venous pressure in the pelvis is set to be lower than the venous pressure outside the pelvis, and the anticancer agent in the pelvis is removed with a dialysis device in a closed circulation immediately after completion of the treatment, in a case where the rate at which a liquid containing drugs and/or blood is drained from a patient is set to be higher than the rate at which the liquid finally obtained is fed to the patient during the perfusion in the pelvis, the blood from the patient is accumulated in an extracorporeal reservoir along with the progress of the perfusion in the pelvis, and the blood finally obtained is required to be returned to the patient after the operation, however, a transfusion device switching unit is provided, and therefore, autologous blood transfusion can be performed by purifying the liquid in the reservoir and returning the purified liquid to the patient, and there is no need to perform the allogeneic blood transfusion. Therefore, infections and post-transfusion graft versus host disease (GVHD) associated with allogeneic blood transfusion, and most of the side effects associated with allogeneic immunity can be avoided. Further, also to patients who do not wish to perform allogeneic blood transfusion because of religious reasons or the like, the drug isolated pelvic perfusion therapy can be applied.

In addition, after completion of the drug isolated pelvic perfusion therapy, a liquid containing drugs and blood accumulated in the reservoir is purified and the purified liquid can be returned into the body of the patient, and therefore, the leakage of the drug from the pelvis to the whole-body system outside the pelvis in the drug isolated pelvic perfusion therapy can be further suppressed. As a result, during the drug isolated pelvic perfusion therapy, a drug in an amount larger than before can be administered into the pelvis, and the effect of the drug isolated pelvic perfusion therapy can be further enhanced.

Further, the perfusion device is provided with a dialysis unit equipped with a dialysis drainage tube and a dialysis return tube each with the tip placed at a position closer to the heart side than the inferior vena cava occlusion unit of the inferior vena cava, an extracorporeal hemodialysis device connectable to the dialysis drainage tube and the dialysis return tube, and a dialysis tube constituting a flow path from the dialysis drainage tube to the dialysis return tube through the hemodialysis device, and therefore, the inferior vena cava in the immediately downstream of the pelvic area is occluded, and the blood dialysis becomes possible at a position in the downstream from the occluded position on the heart side, and the leakage of the drug from the pelvis to the whole-body system outside the pelvis can be further suppressed in the drug isolated pelvic perfusion therapy. As a result, during the drug isolated pelvic perfusion therapy, a drug in an amount larger than before can be administered into the pelvis, and the effect of the drug isolated pelvic perfusion therapy can be further enhanced.

In addition, the perfusion device is provided with a dialysis device switching unit for switching a connection of the dialysis tube to the drainage tube and the return tube in the pelvis, and therefore, it becomes possible to switch easily between the case where the blood dialysis is performed at a position in the immediately downstream of the vein in the pelvic area and the case where the blood dialysis is performed in the pelvic area.

As a result, for example, during the operation of the drug isolated pelvic perfusion therapy, the blood dialysis is performed at a position in the immediately downstream of the vein in the pelvic area, and after completion of the drug isolated pelvic perfusion therapy, the drug remaining in the pelvis can be removed by performing blood dialysis in the pelvic area.

At this time, the dialysis drainage tube and the dialysis return tube are provided with a drainage lumen equipped with an insertion hole for drainage on the distal tip side and a return lumen equipped with an insertion hole for return on the distal tip side, respectively, and may include a catheter having an effective length of 23 cm or more and 50 cm or less and an outer diameter of 3.3 mm or more and 4.7 mm or less.

Since the constitution is as described above, even if a catheter is inserted from the common jugular vein, the subclavian vein, the internal jugular vein, or the like, the catheter can reach the position immediately above the pelvic area of the inferior vena cava, and the leakage of the drug from the pelvic area can be more reliably performed.

At this time, the pelvic perfusion unit may be provided with a control unit for controlling the perfusion pump so that a flow rate of a liquid flowing through the drainage tube is higher by from 20 to 40 ml/min than a flow rate of a liquid flowing through the return tube.

Since the constitution is as described above, a negative-balanced isolated pelvic perfusion (NIPP) method in which the venous pressure in the pelvis is set to be lower than the venous pressure outside the pelvis, and the anticancer agent in the pelvis is removed with a dialysis device in a closed circulation immediately after completion of the treatment can be realized, and in the drug isolated pelvic perfusion method, the leakage of the anticancer agent to the developed collateral circulation can be prevented.

Further, the operation process of a postoperative blood transfusion device and a dialysis device for the inside of the pelvis, may be provided with: a pelvic dialysis process of operating the hemodialysis device in a state that the hemodialysis device is connected to the drainage tube and the return tube in the pelvis; a process of operating a unit for removing the pelvic area closing unit; and a whole body dialysis process of operating the hemodialysis device in a state that the pelvic area closing unit is removed.

Since the constitution is as described above, at first, in a pelvic dialysis process, the dialysis in the pelvis is performed in a state that the hemodialysis device is connected to the drainage tube and the return tube in the pelvis, next, in a process of operating a unit for removing the pelvic area closing unit, the closure of the pelvis is released, and then in a whole body dialysis process, whole body dialysis in which the hemodialysis device operates in a state that the pelvic area closing unit is removed can be performed. Therefore, after completion of the drug isolated pelvic perfusion method, at first, the dialysis in the pelvis is performed with the pelvis closed, and then the closure is released and the dialysis of the whole body is performed, and therefore, after completion of the drug isolated pelvic perfusion method, the drug can be efficiently removed.

At this time, the operation process of a perfusion pump for the pelvis and a dialysis device for the outside of the pelvis may be performed for from 20 to 40 minutes, the pelvic dialysis process may be performed for from 10 to 20 minutes, and the whole body dialysis process may be performed for from 20 to 40 minutes.

Advantageous Effects of Invention

According to the present invention, the perfusion device is provided, between the reservoir of the perfusion tube and the return tube, with a transfusion device switching unit for switching a connection of the transfusion device tube to the downstream side of the reservoir of the perfusion tube, and therefore, a liquid containing drugs and/or blood stored in the reservoir is purified with an autotransfusion device by performing perfusion in the closed pelvis after completion of the perfusion in the pelvis, and the liquid finally obtained can be returned into the body of a patient.

Therefore, for example, in a negative-balanced isolated pelvic perfusion method in which the venous pressure in the pelvis is set to be lower than the venous pressure outside the pelvis, and the anticancer agent in the pelvis is removed with a dialysis device in a closed circulation immediately after completion of the treatment, in a case where the rate at which a liquid containing drugs and/or blood is drained from a patient is set to be higher than the rate at which the liquid finally obtained is fed to the patient during the perfusion in the pelvis, the blood from the patient is accumulated in an extracorporeal reservoir along with the progress of the perfusion in the pelvis, and the blood is required to be returned to the patient after operation, and in this regard, since a transfusion device switching unit is provided, autologous blood transfusion can be performed by purifying the liquid in the reservoir and returning the purified liquid to the patient, and there is no need to perform the allogeneic blood transfusion. Therefore, infections and post-transfusion graft versus host disease (GVHD) associated with allogeneic blood transfusion, and most of the side effects associated with allogeneic immunity can be avoided. Further, also to patients who do not wish to perform allogeneic blood transfusion because of religious reasons or the like, the drug isolated pelvic perfusion therapy can be applied.

In addition, after completion of the drug isolated pelvic perfusion therapy, a liquid containing drugs and blood accumulated in the reservoir is purified and the purified liquid can be returned into the body of the patient, and therefore, the leakage of the drug from the pelvis to the whole-body system outside the pelvis in the drug isolated pelvic perfusion therapy can be further suppressed. As a result, during the drug isolated pelvic perfusion therapy, a drug in an amount larger than before can be administered into the pelvis, and the effect of the drug isolated pelvic perfusion therapy can be further enhanced.

DESCRIPTION OF EMBODIMENTS

Hereinafter, a perfusion device and a method for operating the perfusion device, according to one embodiment of the present invention will be described with reference to FIGS. 1 and 2.

In the present specification, the expression "liquid" is referred to a generic term for all of the liquids that fill vessels or fill between tissues and cells in an animal body, and includes body fluids such as blood, lymph, and cerebrospinal fluid. Further, there may also be a case where a drug such as an anticancer agent or a gene therapeutic agent is included.

In the present embodiment, as the drug, any drug including a drug made of a low-molecular organic compound, a hormonal agent such as erythropoietin, a protein formulation (biopharmaceutical product) such as an antibody preparation, an anticancer agent, a gene therapeutic agent, a nucleic acid medicine such as an antisense, an aptamer, a siRNA, a miRNA, or a decoy, or the like, can be used.

According to a gene introduction method, the gene therapeutic agents can be classified into two types of in vivo gene therapy in which a gene for treatment is administered directly to a living body, and ex vivo gene therapy in which a target cell is taken out of a living body once, a gene is introduced into the cell, and then the resultant cell is returned to the body again as a cell for treatment, and as the gene therapeutic agent of the present invention, either type of the gene therapeutic agents can be used.

As the gene in the in vivo gene therapy, in addition to mda-7/IL-24, which is known as a tumor suppressor gene and suppresses tumor growth by inducing apoptosis when introduced into a tumor cell, various tumor suppressor genes including p53, interferon β, herpes virus thymidine kinase (HSV-tk), interferon-β, interleukin-12 (IL-12), and a tumor suppressor REIC (reduced expression in immortalized cells)/Dickkopf-3 (Dkk-3) can be used.

Further, although these genes may be used as they are, if these genes are used by being inserted into a vector such as a retroviral vector, a lentiviral vector, an adenoviral vector, an adeno-associated virus vector, a Sendai virus vector, or a plasmid vector, the genes are suitable because the gene transfer efficiency is improved.

In addition, as the ex vivo gene therapy, an adoptive immunity gene therapy by using an autologous T cell to which a T-cell receptor gene recognizing a cancer antigen or a chimeric receptor gene binding an antigen recognition site of a cancer antigen-specific antibody to a T-cell activation region is introduced can also be applied in the present invention.

For example, as the T-cell receptor (TCR) gene therapy in which a T-cell receptor gene recognizing a cancer antigen is introduced into a T cell of a patient, a therapy in which a T-cell antigen receptor gene recognizing a MAGE-A4 antigen is introduced in vitro into a lymphocyte derived from peripheral blood of a cancer patient to be treated by using a retroviral vector and then the resultant gene is infused into the patient, or the like can be mentioned.

In the present specification, the expression "proximal side" is referred to as the outside of a living body, that is, the side of a practitioner, in a state that a medical device such as a catheter and sheaths are inserted into the living body, and the expression "distal side" is referred to as the tip side of the portion inserted into a living body, that is, the side of a tissue to be treated.

<Perfusion Device S>

Figure 1:
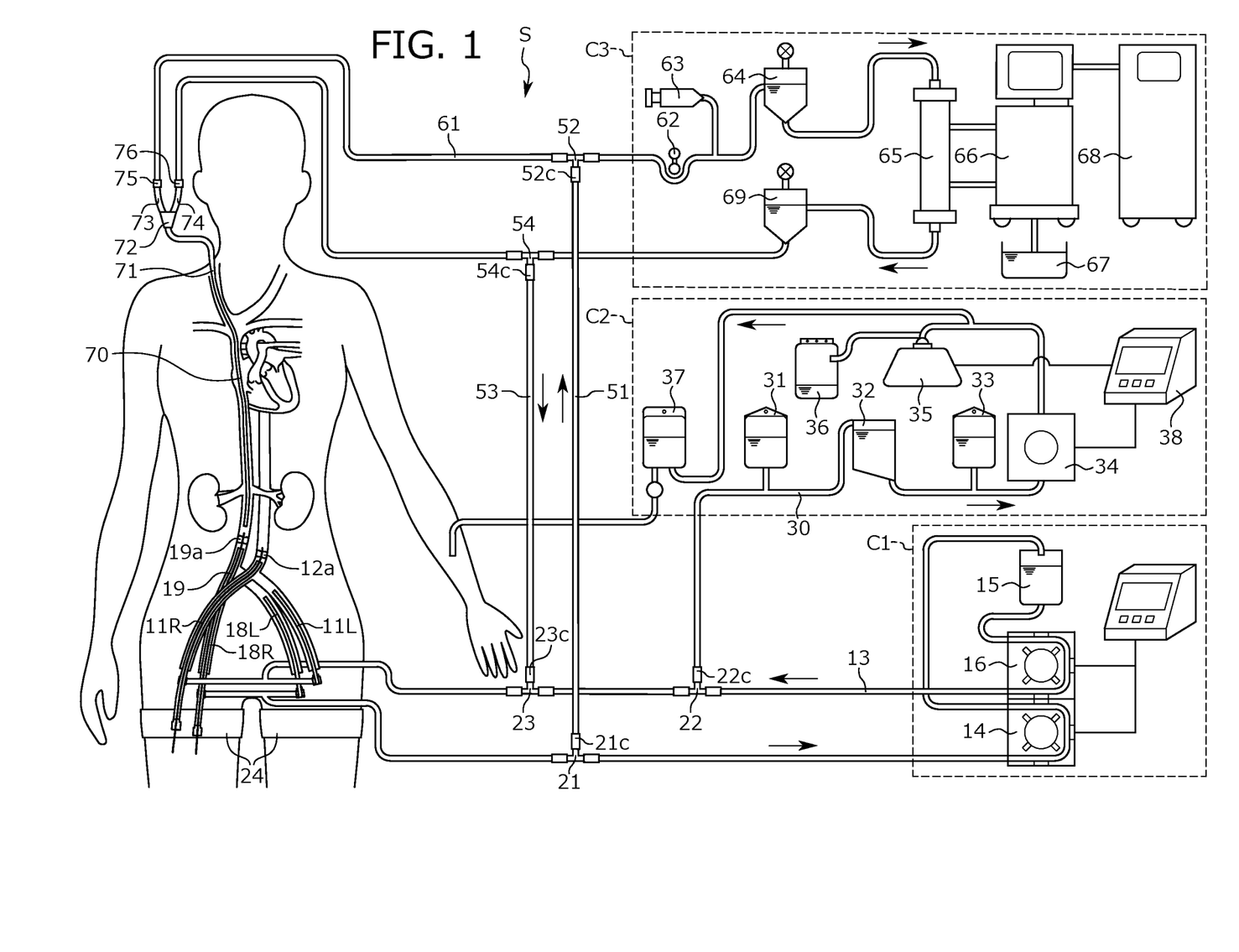
FIG. 1 is a schematic illustration diagram of a perfusion device according to one embodiment of the present invention.

FIG. 1 is a schematic illustration diagram of a perfusion device S according to the present embodiment.

The perfusion device S according to the present embodiment is a device for perfusing a drug such as an anticancer agent in the pelvis by a negative-balanced isolated pelvic perfusion (hereinafter, also referred to as "NIPP") method.

The NIPP is a method in which the venous pressure in the pelvis is set to be lower than the venous pressure outside the pelvis for the purpose of preventing the leakage of a drug to the developed collateral circulation, and the drug in the pelvis is removed with a dialysis device in a closed circulation immediately after completion of the treatment, in the isolated pelvic perfusion therapy in which the aorta and the inferior vena cava are temporarily blocked with balloon catheters and at the same time a blood flow of the lower limbs is temporarily occluded by a pair of tourniquets to block a blood flow in the pelvis part, a drug such as an anticancer agent is injected into the pelvis part, and sucked, the drug concentration in the pelvis is kept high, and the leakage of the drug to the outside of the pelvis is suppressed as far as possible.

In the pelvis, the bladder, the rectum, the uterus and fallopian tube, the lymph nodes, and the like are positioned, and these tissues are application targets of the perfusion device and operation method thereof according to the present embodiment.

As shown in FIG. 1, the perfusion device S according to the present embodiment is provided with a NIPP circuit C1 for administering a drug in the pelvis in a closed circulation, an autotransfusion circuit C2 for purifying a liquid containing blood and drugs, which is accumulated in an extracorporeal reservoir 15 because of the blood removal rate is higher than the blood return rate in the NIPP, after the NIPP operation, and for returning the purified liquid to the outside of the pelvis, and a drug removal circuit C3 for performing blood dialysis outside the pelvis during the NIPP operation, and for performing blood dialysis in the pelvis and the whole body after the NIPP operation.

The NIPP circuit C1 is a circuit for circulating a blood through the femoral artery and femoral vein in the pelvis closed by blocking the blood flow in the femoral region with a pair of tourniquets 24 and blocking the parts immediately above the aortic bifurcation and immediately above the vena caval bifurcation with balloon catheters 12 and 19, and the circuit is filled with a drug during the NIPP operation.

As shown in FIG. 1, the NIPP circuit C1 is provided with: sheaths 18L and 18R as the drainage tubes, which are formed of cannula sheaths and are inserted percutaneously into the left and right femoral veins, respectively; a balloon catheter 19 inserted into the sheath 18R, and of which a balloon 19a is indwelled immediately above the vena caval bifurcation through which blood flows out of the pelvis; a tube 13 for the blood drained from the sheaths 18L and 18R; a blood-flow probe (not shown) for measuring the flow rate of the blood drained from the sheaths 18L and 18R; a pump 14 for feeding the blood drained from the sheaths 18L and 18R to a reservoir 15; the reservoir 15 for storing the blood drained from the sheaths 18L and 18R, and further which is equipped with a drug port (not shown) for mixing a drug with the blood; a pump 16 for delivering the blood from the reservoir 15; a blood-flow probe (not shown) for measuring the flow rate of the blood fed to the sheaths 11L and 11R with the pump 16; the sheaths 11L and 11R as the return tubes, which are formed of a 9-French cannula sheath and a 6-French (or 5-French) cannula sheath and are inserted percutaneously into the left and right femoral arteries, respectively; and a balloon catheter 12 of which a balloon 12a is indwelled immediately above the aortic bifurcation through which blood flows into the pelvis.

The balloon catheters 12 and 19 are provided with balloons 12a and 19a that are dilation tools in distal parts, respectively, and provided with inflation fluid lumens (not shown) for distributing a gas or liquid that expands the balloons 12a and 19a in the lumens.

The blood-flow probe (not shown) is a known blood-flow probe such as an ultrasonic blood flow meter, is connected to a blood flow meter (not shown) with a cable (not shown), and transmits the signals of blood flow rate detected by the blood-flow probe to the blood flow meter.

The tube 13 is made of a known tube for blood vessel, both ends of the tube 13 are connected to the sheaths 18L and 18R and the sheaths 11L and 11R, and the pumps 14 and 16 and the reservoir 15 are connected between the sheaths 18L and 18R and the sheaths 11L and 11R so as to be able to feed a liquid.

Further, a three-way stopcock 21 is attached to the tube 13 in the upstream of the pump 14, and three-way stopcocks 22 and 23 are attached to the tube 13 in the downstream of the pump 16.

By switching the three-way stopcock 21 to a side tube 21c and switching a three-way stopcock 52 to a side tube 52c, the blood flow drained from the sheaths 18L and 18R can be introduced to a drug removal circuit C3 via a switching tube 51.

Further, by switching the three-way stopcock 23 to a side tube 23c and switching a three-way stopcock 54 to a side tube 54c, the blood flow from a drug removal circuit C3 can be introduced to the sheaths 11L and 11R via a switching tube 53.

In addition, by switching the three-way stopcock 22 to a side tube 22c, the blood flow from the reservoir 15 can be introduced to an autotransfusion circuit C2.

As the autotransfusion circuit C2, a known recovery-type autologous blood transfusion system typified by Cell Saver (registered trademark) or the like is used.

In the autotransfusion circuit C2 of the present embodiment, after completion of the NIPP treatment in which a drug is administered into the pelvis, a liquid containing drugs and blood, which is drained from the pelvis, is purified to remove the drug by using a system to be used for recovery-type autologous blood transfusion, and then the purified liquid is injected into the vein outside the pelvis of a patient.

Blood transfusions are roughly classified into allogeneic blood transfusion in which blood from another individual is transfused, and autologous blood transfusion in which blood from the patient him/herself is transfused.

In the autologous blood transfusion, the blood required for the transfusion is supplied with the own blood, and therefore, infections and post-transfusion graft versus host disease (GVHD) associated with allogeneic blood transfusion, and most of the side effects associated with allogeneic immunity can be avoided.

The autologous blood transfusion is roughly classified into three methods of a blood collection and dilution method immediately before operation (dilution method), a bleeding recovery method (recovery method), and a blood-storage type autotransfusion method (blood storage method).

The dilution method is a method in which after general anesthesia is started in an operating room, around 1,000 ml of autologous blood is collected at one time, and then infusion in a volume corresponding to the volume of the collected blood is performed to dilute the blood in the body of a patient. At the end of the operation, the collected autologous blood is returned to the patient.

The recovery method is a method in which the blood bled during the operation and after the operation is recovered and returned to the patient. There are an intraoperative recovery method in which the blood bled during the operation is recovered by suction, unnecessary ones are removed with a centrifugal separator, and only the red blood cells are returned, and a postoperative recovery method in which the blood bled after the operation is returned through a filter as it is.

The blood storage method is a method in which blood is collected 2 to 3 times before the operation, and the collected blood is transfused to a patient during the operation or after the operation.

The autotransfusion circuit C2 is provided: with a tube 30 with the end part on the upstream side connected to a side tube 22c of a three-way stopcock 22 and the end part on the downstream side connected to the vein of the arm of a patient; and with a physiological saline bag 31 containing an anticoagulant agent, a reservoir for recovery 32, a physiological saline bag for washing 33, a roller pump 34 for feeding a liquid containing blood and drugs through the tube 30, a centrifugal bowl 35, a waste liquid bag 36 for storing the unnecessary substances removed with the centrifugal bowl, a re-transfusion bag 37 for storing a liquid containing the blood to be returned to the patient, separated with the centrifugal bowl, and a controller 38 for controlling the roller pump 34 and the centrifugal bowl 35, which are connected in order between both end parts of the tube 30.

The centrifugal bowl 35 is a device that is equipped with a bowl rotating at a high speed, and separates blood into respective components by the differences in the specific gravity. The red blood cells having the largest specific gravity form a layer on the outer side of the bowl, and other plasma components having a small specific gravity form a layer on the inner side of the bowl. After the red blood cells are concentrated until the hematocrit value in the bowl reaches from 50 to 60%, physiological saline is injected into the centrifugal bowl, and free hemoglobin contained in the plasma components, activated coagulation factors, a large amount of anticoagulant agent, an anticancer agent and the like, which are substances inconvenient for returning with the blood to a patient, are washed off, to obtain a washed concentrated red blood cell liquid.

During the NIPP operation, since the speed of draining from the sheaths 18L and 18R is kept faster than the speed of returning to the sheaths 11L and 11R, a liquid containing blood and drugs in a volume corresponding to the speed difference accumulates in the reservoir 15. In view of this, after the NIPP operation, the three-way stopcock 22 of the NIPP circuit C1 is switched to the side tube 22c, a liquid containing blood and drugs, which is flowed out from the reservoir 15 and is led from the side tube 22c, is sucked by a roller pump 34 from the physiological saline bag 31 with the addition of an anticoagulant agent such as heparin, the sucked liquid is fed to the centrifugal bowl 35, and the drugs and the like are washed off with the centrifugal bowl 35 to obtain a washed concentrated red blood cell liquid. This washed concentrated red blood cell liquid is stored in the re-transfusion bag 37, and then is returned to the vein of the arm of a patient.

The drug removal circuit C3 is provided with a hemodialysis device, and is a circuit that performs blood dialysis outside the pelvis during drug administration and performs blood dialysis in the pelvis after completion of drug administration.

As shown in FIG. 1, the drug removal circuit C3 is provided with a double-lumen dialysis indwelling catheter 70 indwelled by being inserted through the right common jugular vein of a patient so that the tip of the catheter is placed in the inferior vena cava, and a tube 61 connected to a port 75 on the blood removal side, continuously connected to a blood removal lumen leading to a side hole 77b on the distal side of the dialysis indwelling catheter 70. To the tube 61, a pump 62, a syringe for anticoagulant injection 63, an arterial drip chamber 64, a dialyzer 65, a hemodialysis monitor 66, a waste liquid tank 67, a dialysate supply device 68, and a venous drip chamber 69, are connected in order. On the blood supply side of the tube 61, a port 76 on the blood supply side is connected, continuously connected to a blood supply lumen leading to a side hole 77c on the proximal side of the dialysis indwelling catheter 70.

The dialysis indwelling catheter 70 is used for removing a drug from a liquid containing the blood in the pelvic closure area immediately after completion of NIPP, and for removing a drug from a liquid containing the blood in the whole body after removing the drug in the liquid containing the blood in the pelvic closure area immediately after completion of NIPP. The dialysis indwelling catheter 70 is made of a catheter for vascular access, which is blood access during dialysis, and is an endovascular indwelling catheter called a VAS-CATH (registered trademark) catheter. The vascular access is blood access for removing and returning blood during dialysis, and is performed by inserting a catheter into the femoral vein, the internal jugular vein, or the subclavian vein. An indwelling catheter for emergency blood access, which is used for performing blood supply and blood removal by indwelling the catheter in the blood vessel for the purpose of performing artificial kidney (blood dialysis, filtration of blood, hemodiafiltration, or the like), may be used.

Figure 2:
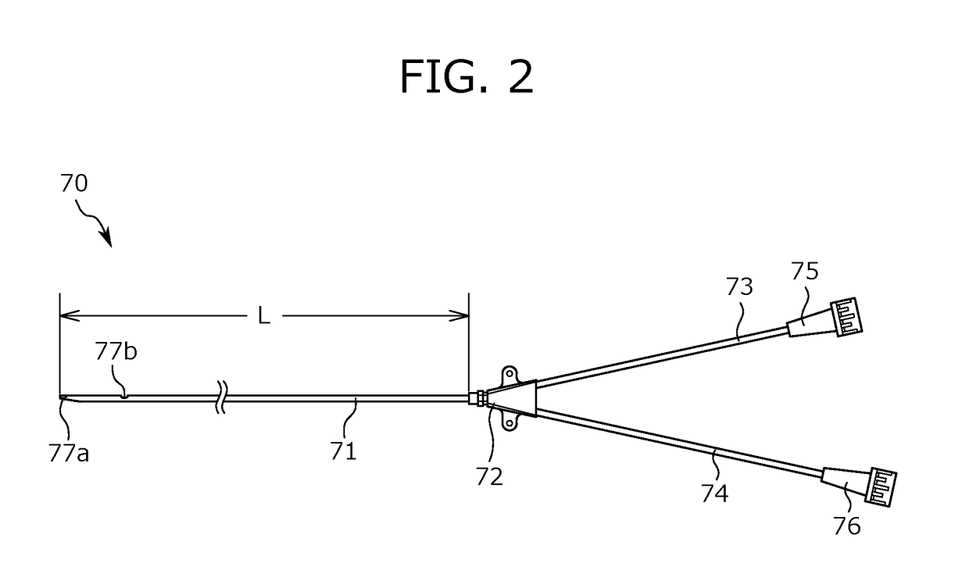
FIG. 2 is a schematic diagram showing a dialysis indwelling catheter for the inferior vena cava according to one embodiment of the present invention.

The dialysis indwelling catheter 70 is a double-lumen catheter having two lumens in the tube, and as shown in FIG. 2, the dialysis indwelling catheter 70 is provided with: a double-lumen catheter body 71; a blood removal branch pipe 73 and a blood supply branch pipe 74, which are connected to the proximal sides of the two lumens of the catheter body 71, respectively; a branch part 72 for connecting the catheter body 71 to the blood removal branch pipe 73 and the blood supply branch pipe 74; and ports 75 and 76 for connecting the tube 61 to the proximal ends of the blood removal branch pipe 73 and the blood supply branch pipe 74, respectively.

The catheter body 71 has two lumens constituted in the lumen of the catheter body with a partition wall (not shown). The two lumens are a blood removal lumen for distributing the blood that is removed from the upstream side at an indwelled position of the catheter body 71 in the inferior vena cava, and a blood supply lumen for distributing the blood that is supplied to the downstream side at an indwelled position of the catheter body 71 in the inferior vena cava. The blood removal lumen is connected to the blood removal branch pipe 73, and the blood supply lumen is connected to the blood supply branch pipe 74.

In the side on the tip side of the catheter body 71, side holes 77a and 77b are arranged from the distal side toward the proximal side.

The side hole 77b penetrates the blood removal lumen, and the side hole 77a penetrates the blood supply lumen.

The blood removal side and blood supply side of the tube 61 are connected to the ports 75 and 76, respectively.

It is suitable that the dialysis indwelling catheter 70 has an effective length L of 23 cm or more and 50 cm or less, preferably 25 cm or more and 45 cm or less, and furthermore preferably 30 cm or more and 40 cm or less. When the effective length L is 30 cm or more and 40 cm or less, the side holes 77a and 77b can surely reach the inferior vena cava, and therefore, the amount of a drug such as an anticancer agent, which leaks from the NIPP circuit C1, can be reduced to from ½ to ⅓ of the amount in a case where the dialysis indwelling catheter having an effective length of 20 cm is used.

For example, in a patient having a body height of 174 cm, the dialysis indwelling catheter 70 having an effective length of 25 cm does not reach the inferior vena cava, and therefore, the effective length of the dialysis indwelling catheter 70 is 30 cm or more when considering the versatility so that the dialysis indwelling catheter 70 can be used for a patient with a different physique.

The outer diameter (diameter) of the dialysis indwelling catheter 70 is preferably 10-French (3.3 mm) or more and 14-French (4.7 mm) or less. If the outer diameter is less than 10-French, it becomes difficult to ensure the blood volume required for dialysis. The outer diameter of the dialysis indwelling catheter 70 is suitably 11-French (3.7 mm) or more and 13-French (4.3 mm) or less, more suitably 11.5-French (3.8 mm) or more and 12.5-French (4.2 mm) or less, and furthermore preferably 12-French (4.0 mm).

In this regard, the expression "effective length L" is referred to as a length also called an insertion length, and is a length from the tip on the distal side to the tip side of the branch part 72.

Further, on the blood removal side of the tube 61, a three-way stopcock 52 is provided between the port 75 on the blood removal side and the pump 62, and a switching tube 51 connected to the three-way stopcock 21 on the drainage side of the tube 13 in the NIPP circuit C1 is connected.

On the blood supply side of the tube 61, a three-way stopcock 54 is provided between a venous drip chamber 69 and the port 76 on the blood supply side, and a switching tube 53 connected to the three-way stopcock 23 on the liquid-feeding side of the tube 13 in the NIPP circuit C1 is connected.

The dialyzer is referred to as an artificial device with which blood is taken out of the body, the dialysis is performed between the blood and a dialysate by using a semipermeable membrane, the electrolyte is corrected, the water content is corrected, and impurities are removed, etc., in order to purify the blood, and the purified blood is returned to the body.

The hemodialysis monitor is referred to as a device with which the dialysate is controlled in order to remove excess water and waste products, and the condition of a patient is monitored.

<NIPP (Negative-Balanced Isolated Pelvic Perfusion)>

By taking as an example the case where cancer has developed in the pelvis and perfusion with an anticancer agent is performed, the NIPP realized by a perfusion device S of the present embodiment will be described with reference to FIG. 1.

NIPP Treatment Preparation (Operating Room)

The procedures for insertion of all of the sheaths and catheters are percutaneously performed in a minimally invasive manner. A central venous catheter (not shown) is inserted into the internal jugular vein, fluid-replacement and transfusion routes are secured, and at the same time, the central venous pressure (CVP) is monitored.

A pair of tourniquets 24 are wound around both femoral regions in advance.

Sheaths 11L and 11R and sheaths 18L and 18R formed of 9-French cannula sheaths and 6-French (or 5-French) cannula sheaths are inserted through the left and right femoral arteries and the left and right femoral veins, respectively by a Seldinger technique.

A dialysis indwelling catheter 70 is inserted into the right common jugular vein. In the present embodiment, a dialysis indwelling catheter 70 is inserted into the right common jugular vein, but the dialysis indwelling catheter 70 may be inserted into the left common jugular vein, or may be inserted into the internal jugular vein or the subclavian vein. The dialysis indwelling catheter 70 is indwelled so that the tip of the catheter is placed in the inferior vena cava. In this way, a drug (anticancer agent) leaking from the closed NIPP circuit C1 during the NIPP operation is not returned to the heart, and can be prevented from entering the systemic circulation.

A tube 61 of the drug removal circuit C3 is connected to the dialysis indwelling catheter 70. Switching tubes 51 and 53 are connected to three-way stopcocks 52 and 54 of the tube 61, respectively. The drug removal circuit C3 is connected to the NIPP circuit C1 by the switching the tubes 51 and 53.

Heparin is intravenously administered in the required amount (120 U/kg as a guide) so that the activated clotting time (ACT) is at least 200 seconds or more.

Balloon catheters 12 and 19 are inserted one by one through the sheaths 11R and 18R of the right femoral artery and right femoral vein, respectively, and the arterial balloon catheter 12 is indwelled so that a balloon 12a is placed immediately above the abdominal aortic bifurcation, and the venous balloon catheter 19 is indwelled so that a balloon 19a is placed immediately above the confluence point on both sides of iliac veins of the inferior vena cava.

After confirming that the ACT has reached 200 seconds or more, both of the femoral regions are pressurized with the pair of tourniquets 24 to block the blood flow to the lower limbs. At this time, as the blood pressure at the time of pressurization by the pair of tourniquets 24, the systolic blood pressure of +100 mmHg is basically used. In this regard, the normal blood pressure is around 250 mmHg.

The blood flow to the lower limbs is blocked, and then in the order of the balloon catheter 12 in the aorta, and the balloon catheter 19 in the inferior vena cava, the balloon catheters 12 and 19 are inflated to occlude and block the aorta and the vena cava, respectively. With the above procedures, the NIPP circuit C1 that serves as a pelvic closed circuit is completed.

Next, instruments and tools of from a physiological saline bag 31 to a re-transfusion bag 37 are connected to the tube 30, and a controller 38 is connected to arrange the autotransfusion circuit C2. The blood removal side of the tube 30 is connected to the blood supply side of the tube 13 of the NIPP circuit C1, with a three-way stopcock 22, and the blood supply side of the tube 30 is connected to the venous side of the forearm of a patient, for example, the basilic vein, the cephalic vein or the like, to complete the autotransfusion circuit C2. In this regard, the vein to be connected may be any vein as long as it is transfusable, and is not limited to the basilic vein or the cephalic vein.

Isolated pelvic angiography is performed in a closed circulation with an injection rate of 5.5 ml/sec and an injection volume of 40 ml from side arms of the sheaths 11L and 11R inserted into both of the left and right femoral arteries. At this time, at the same time, suction is performed at a suction rate of 6 ml/sec in total from both of the side arms of the sheaths 18L and 18R inserted into the left and right femoral veins.

No visualization of the iliolumbar artery outside the pelvis is confirmed in the isolated pelvic angiography, and the presence or absence of visualization (outflow of the contrast agent) of an arterial system outside the pelvis, in particular, the lumbar artery is checked. If it is confirmed that there is no visualization, the rate at that time can be regarded as the basic injection rate in the NIPP.

If there is no outflow of the contrast agent to the outside of the pelvis, the basic perfusion rates are set to be an injection rate of around 330 ml/min and a suction rate of around 355 ml/min (the difference of the suction rate– the injection rate is basically set to be 25 ml/min). Further, in a case where the outflow of the contrast agent to the outside of the pelvis is observed through a side return path (arterial collaterals or arterial anastomoses), the inflow rate is decreased (the lower limit is 5.0 ml/sec), the isolated pelvic angiography is performed again as needed in the pelvis, and the injection rate is determined by conducting the above examination. The injection rate can be set to 6 ml/sec at most in consideration of the relationship with the injection pressure. In a case where the injection rate is to be increased, the isolated pelvic angiography is performed again at a desired injection rate, and the presence or absence of the anastomosis with the extrapelvic arterial system is checked.

It is confirmed by isolated pelvic angiography that the balloon catheter in the inferior vena cava is sufficiently inflated, and there is no venous collateral circulation from the pelvis to the outside of the pelvis.

NIPP Treatment (Operating Room)

When the injection rate in the NIPP is determined, all the pressure of the balloons 12a and 19a of the balloon catheters 12 and 19 and the pressure of the pair of tourniquets 24 are released, and four sheaths 11L, 11R, 18L, and 18R, and pumps 14 and 16 (cardiopulmonary circulation devices) are connected with a tube 13 that serves as a drug administration circulation system circuit to construct a perfusion system of the NIPP circuit C1.

The color of the urine is checked, and in a case where the urine is not transparent, the urine is waited until the color becomes transparent, and the fluid replacement is increased as needed. The reason for waiting until the urine becomes transparent is to prevent the reabsorption of an anticancer agent in the renal tubule.

When it is confirmed that the color of the urine is transparent, both of the femoral regions are pressurized (normally 250 mmHg) again with a pair of tourniquets 24 to block the blood flow to the lower limbs, and the pumps 14 and 16 are activated to start the perfusion in the pelvis.

Next, when the aorta is blocked again with the balloon 12a of the balloon catheter 12 and the aorta is blocked, the suction rate of the pump 14 for drainage is set to be higher than the injection rate of the pump 16 for liquid feeding by around 25 ml/min.

When the flow rate of blood in the tube 17 is stabilized, the inferior vena cava is occluded with the balloon 19a of the balloon catheter 19 to make the inside of the pelvis to be in a closed circulation. At this time, if there is no outflow of the contrast agent to the outside of the pelvis, the basic perfusion rates are set to be an injection rate of around 330 ml/min with the pump 16 for liquid feeding, and a suction rate of around 355 ml/min with the pump 14 for drainage. That is, the difference of the suction rate– the injection rate is basically set to be 25 ml/min.

An anticancer agent is injected into a reservoir 15 in the NIPP circuit C1, and the anticancer agent is injected into and sucked out of the pelvis by using the pumps 14 and 16. The injection and suction are performed for 30 minutes. Immediately after administration of the first anticancer agent, indigo carmine is administered to the reservoir 15, and then by monitoring the color of the indigo carmine discharged into the urine, the leakage of the anticancer agent to the outside of the pelvis is indirectly grasped. The total cisplatin dosage is divided into three equal doses, and each dose is administered in 0, 5, and 10 minutes after the NIPP perfusion as the administration interval, and perfusion is performed for 30 minutes.

During the NIPP treatment, the urine volume is checked, and reported to an anesthesiologist as needed. If the urine volume is 10 ml/min or less, the fluid replacement is increased, and a diuretic agent is administered as needed.

Immediately after completion of the drug administration circulation in the NIPP circuit C1, by switching the three-way stopcocks 21 and 23 to the side tubes 21c and 23c, and by switching the three-way stopcocks 52 and 54 to the side tubes 52c and 54c, the switching to the drug removal circuit C3 is conducted. The drug removal (at a rate of around 300 ml/min) is performed in an isolated pelvic circulation, and the anticancer agent in the pelvis is removed for 15 minutes.

By switching the NIPP circuit C1 to the drug removal circuit C3, and at the same time by switching the three-way stopcocks 22 arranged in the downstream of the reservoir 15 of the NIPP circuit C1 and in the upstream of the three-way stopcock 23 to the side tubes 22c, the switching to the autotransfusion circuit C2 is conducted.

By using a centrifugal bowl 35, the blood containing the anticancer agent in the reservoir 15 is purified with the autotransfusion circuit C2, and at the same time as the purification, the blood from which the anticancer agent has been removed is injected into the vein of a patient.

After removing the anticancer agent in the pelvis for 15 minutes with the drug removal circuit C3, the balloon catheters 12 and 19 and the pair of tourniquets 24 are released in this order, and the drug removal is performed for 30 minutes under the systemic circulation.

After completion of the drug removal circulation, an appropriate amount of heparin antagonist (protamine) is administered to return the ACT to the preoperative level, and then the sheaths 11L, 11R, 18L, and 18R are removed, and the hemostasis is performed.

After the hemostasis is confirmed, awakening from the anesthesia is performed.

After the patient is returned to a ward, the rest time of the patient on a bed is usually set to 6 hours.

From the above, the perfusion method achieved by the perfusion device S of the present embodiment is a perfusion method in the pelvis, which is used for recovering a liquid containing drugs and/or blood from a drainage tube for connecting to the vein and used for injecting the liquid finally obtained into a return tube for connecting to the artery, in a state that the pelvis is closed from the outside of the pelvis by blocking a blood flow in the artery from the heart side to the pelvis side and a blood flow of the inferior vena cava from the pelvis side to the heart side with balloon catheters, respectively and by blocking a blood flow from the pelvis side to the lower-limb side with a pair of tourniquets.

In this perfusion method in the pelvis, a circuit formation process of forming a circuit of the liquid is performed,
in the circuit formation process,
a step of forming a NIPP circuit from the drainage tube to the return tube through the perfusion pump and the reservoir, by connecting, with a perfusion tube, a perfusion pump for recovering the liquid from the drainage tube and injecting the liquid finally obtained into the return tube to a reservoir for storing a part of the liquid from the drainage tube,
a step of forming an autotransfusion circuit by connecting, with a transfusion device tube, an autotransfusion tube for connecting to the vein outside the pelvis to an autotransfusion device, and
a step of occluding the inferior vena cava at a position between the balloon catheter and the heart, arranging a dialysis drainage tube and a dialysis return tube so that the tips are placed at a position on the opposite side of the heart in the inferior vena cava than the occluded position above, and forming a drug removal circuit from the dialysis drainage tube to the dialysis return tube through the hemodialysis device with a dialysis tube, are performed.

After the circuit formation process,
a pelvic perfusion and extrapelvic dialysis process of injecting the liquid finally obtained into the return tube while recovering the liquid from the drainage tube by using the perfusion pump, and at the same time, recovering the liquid from the dialysis drainage tube and removing a drug contained in the liquid with the hemodialysis device, and injecting the liquid from which the drug has been removed into the dialysis return tube,
a switching process of switching a connection of the transfusion device tube to the downstream side of the reservoir of the perfusion tube between the reservoir of the perfusion tube and the return tube, and switching a connection of the dialysis tube to the drainage tube and the return tube in the pelvis, and a postoperative autologous blood transfusion and postoperative pelvic dialysis process of purifying the liquid stored in the reservoir and returning the purified liquid to the vein outside the pelvis with the autotransfusion device, and further purifying the liquid in the pelvis with the hemodialysis device, are performed.

<Method for Operating Perfusion Device S>

Next, a method for operating a perfusion device S of the present embodiment will be described.

A perfusion device S shown in FIG. 1 is arranged on a patient, and then a method for operating the perfusion device S of the present embodiment is performed.

First, operation processes of perfusion pumps for the pelvis (pumps 14 and 16), and dialysis devices for the outside of the pelvis (a hemodialysis monitor 66 and a dialysate supply device 68) are performed.

These processes operate in a state that the pumps 14 and 16 are connected to the sheaths 18L and 18R and the sheaths 11L and 11R in the pelvis. At the same time, the hemodialysis monitor 66 and the dialysate supply device 68 operate in a state of being connected to a blood removal branch pipe 73 and a blood supply branch pipe 74 of a dialysis indwelling catheter 70.

In this way, the liquid in the pelvis, which contains blood and drugs and is drained from the sheaths 18L and 18R, is perfused in the NIPP circuit C1, and at the same time the liquid containing the blood outside the pelvis is dialyzed in the indwelled position of the dialysis indwelling catheter 70, and the NIPP is performed.

Next, a postoperative flow path switching unit operation process of operating a transfusion device switching unit (three-way stopcock 22), and a dialysis device switching unit (three-way stopcocks 21, 23, 52, and 54) is performed.

In this process, at the end of the NIPP, the three-way stopcock 22 is switched to the side tube 22c.

Further, at the same time, the three-way stopcocks 21, 23, 52, and 54 are switched to the side tubes 21c, 23c, 52c, and 54c.

After that, a postoperative blood transfusion device and pelvic dialysis device operation process of operating an autotransfusion device (centrifugal bowl 35) in a state of being connected to the downstream side of a reservoir 15 of a perfusion tube (tube 13), and further operating hemodialysis devices (a dialyzer 65, a hemodialysis monitor 66, and a dialysate supply device 68) in a state of being connected to a drainage tube (sheaths 18L and 18R) and a return tube (sheaths 11L and 11R) in the pelvis, is performed.

Since a part of the liquid containing blood and drugs drained from the pelvis of a patient is stored in the reservoir 15, by switching the three-way stopcock 22 to the side tube 22c, the liquid is introduced into the autotransfusion circuit C2, and purified in the centrifugal bowl 35, and then the purified liquid is returned to the vein outside the pelvis of the patient.

an autotransfusion device (centrifugal bowl 35) operates in a state of being connected to the downstream side of the reservoir 15 of the perfusion tube (tube 13), and in parallel a pelvic dialysis process, a process of operating a unit for removing the pelvic area closing unit, and a whole body dialysis process are performed.

That is, the pelvic dialysis process, which is operated in a state that the hemodialysis devices (a dialyzer 65, a hemodialysis monitor 66, and a dialysate supply device 68) are connected to a drainage tube (sheaths 18L and 18R) and a return tube (sheaths 11L and 11R) in the pelvis, is performed. That is, the liquid containing blood and drugs in the pelvis of a patient after completion of the NIPP is introduced into the drug removal circuit C3, and dialyzed with a dialyzer 65, and then the dialyzed liquid is returned to the outside of the pelvis of the patient through the dialysis indwelling catheter 70.

After that, a process of operating a unit for removing the pelvic area closing unit (releasing the balloons 12a and 19a and the pair of tourniquets 24) is performed. Next, the whole body dialysis process of operating the hemodialysis devices (a dialyzer 65, a hemodialysis monitor 66, and a dialysate supply device 68) in a state that the pelvic area closing unit is removed (the balloons 12a and 19a and the pair of tourniquets 24 are released) is performed to dialyze the liquid containing the blood of the whole body of the patient.

According to the above, the processing of the method for operating a perfusion device S of the present embodiment is completed.

According to the above-described perfusion device S and method for operating the perfusion device S of the present embodiment, and the NIPP with the use of the perfusion device S, by rapidly removing an anticancer agent from the blood containing the anticancer agent at a high concentration in a reservoir 15 of the NIPP with the autotransfusion circuit C2 together with the completion of the NIPP treatment, and by returning the resultant blood into the body, it is possible to perform the perfusion without blood transfusion or with autologous transfusion of a small volume of blood.

In addition, a dialysis indwelling catheter 70 is inserted into the common jugular vein, and the tip of the catheter is placed in the inferior vena cava. The leaked anticancer agent in the NIPP flows into the inferior vena cava, flows to the heart, and spreads throughout the whole body, and as a result, the kidney is also exposed to the anticancer agent. Therefore, by placing the tip of the dialysis indwelling catheter 70 in the inferior vena cava, the leaked anticancer agent is directly recovered before returning to the heart, and the anticancer agent is removed with the dialysis device.

EXAMPLES

By using the above-described perfusion device S and method for operating the perfusion device S of the present embodiment, in accordance with the method described in <NIPP (negative-balanced isolated pelvic perfusion)>, the NIPP with the use of an anticancer agent was performed on 20 cases, and the degree of the anticancer agent removal was examined. At this time, the operation time of a centrifugal bowl 35 of an autotransfusion circuit C2 was set to 5 minutes.

As a result, 95% on average of the anticancer agent was removed in 5 minutes with the autotransfusion circuit C2. Further, when a liquid containing the blood to be returned to the vein of a patient from a tube 30 of the autotransfusion circuit C2 was confirmed by pathological examination, cancer cells were not detected in all of the cases.

In addition, peripheral blood was collected, and when the anticancer agent concentration of the peripheral blood was measured, it was found that the concentration of the anticancer agent in the peripheral blood was reduced to from ⅓ to ⅖ of the anticancer agent concentration of the peripheral blood in a case where conventional NIPP was performed.

Conventionally, it has not been known that an anticancer agent can be removed with a recovery-type autologous blood transfusion system, and there has been no known case of using an autologous blood transfusion system for the purpose of removing an anticancer agent. However, it has been found that as in the present embodiment, in combination with an autotransfusion circuit C2 using an autologous blood transfusion system in the downstream of a reservoir 15 of a NIPP circuit C1, the anticancer agent can be effectively removed from the liquid containing blood and anticancer agent stored in the reservoir 15 after completion of the NIPP.

REFERENCE SIGNS LIST

C1: NIPP circuit
C2: Autotransfusion circuit
C3: Drug removal circuit
11L, 11R: Sheath
12, 19: Balloon catheter
12a, 19a: Balloon
13, 30, 61: Tube
14, 16, 62: Pump
15: Reservoir
11L, 11R, 18L, 18R: Sheath
21, 22, 23, 52, 54: Three-way stopcock
21c, 22c, 23c: Side tube
24: A pair of tourniquets
31: Physiological saline bag
32: Reservoir for recovery
33: Physiological saline bag for washing
34: Roller pump
35: Centrifugal bowl
37: Re-transfusion bag
38: Controller
51, 53: Switching tube
63: Syringe for anticoagulant injection
64: Arterial drip chamber
65: Dialyzer
66: Hemodialysis monitor
67: Waste liquid tank
68: Dialysate supply device
69: Venous drip chamber
70: Dialysis indwelling catheter
71: Catheter body
72: Branch part
73: Blood removal branch pipe
74: Blood supply branch pipe
75, 76: Port
77a, 77b, 77c: Side hole

The invention claimed is:

1. A perfusion device for recovering a liquid containing a drug and/or blood from a drainage tube for connecting to the inferior vena cava and for injecting the liquid finally obtained into a return tube for connecting to the artery, which is provided with a pelvic area closing unit for closing the inside of the pelvis from the outside of the pelvis by including an artery occlusion unit for blocking a blood flow in the artery from the heart side to the pelvis side, an inferior vena cava occlusion unit for blocking a blood flow of the inferior vena cava from the pelvis side to the heart side, and a lower-limb side blocking unit for blocking a blood flow from the pelvis side to the lower-limb side, comprising:

a pelvic perfusion unit equipped with a perfusion pump for recovering the liquid from the drainage tube and injecting the liquid finally obtained into the return tube, a reservoir for storing a part of the liquid from the drainage tube, and a perfusion tube constituting a flow path from the drainage tube to the return tube through the perfusion pump and the reservoir;

an autotransfusion unit equipped with a transfusion device tube, an autotransfusion device connected to the transfusion device tube, and an autotransfusion tube for connecting to the vein outside the pelvis;

a dialysis unit equipped with a dialysis drainage tube and a dialysis return tube each with the tip placed at a position closer to the heart side than the inferior vena cava occlusion unit of the inferior vena cava, an extracorporeal hemodialysis device connectable to the dialysis drainage tube and the dialysis return tube, and a dialysis tube constituting a flow path from the dialysis drainage tube to the dialysis return tube through the hemodialysis device;

a transfusion device switching unit for switching a connection of the transfusion device tube to the downstream side of the reservoir of the perfusion tube, between the reservoir of the perfusion tube and the return tube; and a dialysis device switching unit for switching a connection of the dialysis tube to the drainage tube and the return tube in the pelvis, between the reservoir of the perfusion tube and the return tube.

2. The perfusion device according to claim 1, wherein the dialysis drainage tube and the dialysis return tube are provided with a drainage lumen equipped with an insertion hole for drainage on the distal tip side, and a return lumen equipped with an insertion hole for return on the distal tip side, respectively, and the perfusion device comprises a catheter having an effective length of 23 cm or more and 50 cm or less and an outer diameter of 3.3 mm or more and 4.7 mm or less.

3. A method for operating a perfusion device for recovering a liquid containing a drug and/or blood from a drainage tube for connecting to the inferior vena cava and for injecting the liquid finally obtained into a return tube for connecting to the artery, which is provided with a pelvic area closing unit for closing the inside of the pelvis from the outside of the pelvis by including an artery occlusion unit for blocking a blood flow in the artery from the heart side to the pelvis side, an inferior vena cava occlusion unit for blocking a blood flow of the inferior vena cava from the pelvis side to the heart side, and a lower-limb side blocking unit for blocking a blood flow from the pelvis side to the lower-limb side, wherein the perfusion device comprises:

a pelvic perfusion unit equipped with a perfusion pump for recovering the liquid from the drainage tube and injecting the liquid finally obtained into the return tube, a reservoir for storing a part of the liquid from the drainage tube, and a perfusion tube constituting a flow path from the drainage tube to the return tube through the perfusion pump and the reservoir;

an autotransfusion unit equipped with a transfusion device tube, an autotransfusion device connected to the transfusion device tube, and an autotransfusion tube for connecting to the vein outside the pelvis;

a dialysis unit equipped with a dialysis drainage tube and a dialysis return tube each with the tip placed at a position closer to the heart side than the inferior vena cava occlusion unit of the inferior vena cava, an extracorporeal hemodialysis device connectable to the dialysis drainage tube and the dialysis return tube, and a dialysis tube constituting a flow path from the dialysis drainage tube to the dialysis return tube through the hemodialysis device;

a transfusion device switching unit for switching a connection of the transfusion device tube to the downstream side of the reservoir of the perfusion tube, between the reservoir of the perfusion tube and the return tube; and a dialysis device switching unit for switching a connection of the dialysis tube to the drainage tube and the return tube in the pelvis, between the reservoir of the perfusion tube and the return tube, and the method performs:

an operation process of a perfusion pump for the pelvis and a dialysis device for the outside of the pelvis, in which the perfusion pump operates in a state of being connected to the drainage tube and the return tube in the pelvis, and the hemodialysis device operates in a state of being connected to the dialysis drainage tube and the dialysis return tube;

an operation process of a postoperative flow path switching unit, in which the transfusion device switching unit and the dialysis device switching unit operate; and an operation process of a postoperative blood transfusion device and a dialysis device for the inside of the pelvis, in which the autotransfusion device operates in a state of being connected to the downstream side of the reservoir of the perfusion tube, and the hemodialysis device operates in a state of being connected to the drainage tube and the return tube in the pelvis.

4. The method for operating a perfusion device according to claim 3, wherein the pelvic perfusion unit is provided with a control unit for controlling the perfusion pump so that a flow rate of a liquid flowing through the drainage tube is higher by from 20 to 40 ml/min than a flow rate of a liquid flowing through the return tube.

5. The method for operating a perfusion device according to claim 3, wherein the operation process of a postoperative blood transfusion device and a dialysis device for the inside of the pelvis, comprises:

a pelvic dialysis process of operating the hemodialysis device in a state that the hemodialysis device is connected to the drainage tube and the return tube in the pelvis;

a process of operating a unit for removing the pelvic area closing unit; and a whole body dialysis process of operating the hemodialysis device in a state that the pelvic area closing unit is removed.

6. The method for operating a perfusion device according to claim 5, wherein the operation process of a perfusion pump for the pelvis and a dialysis device for the outside of the pelvis is performed for from 20 to 40 minutes, the pelvic dialysis process is performed for from 10 to 20 minutes, and the whole body dialysis process is performed for from 20 to 40 minutes.

* * * * *